(12) United States Patent
Kulkarni et al.

(10) Patent No.: US 8,507,465 B2
(45) Date of Patent: Aug. 13, 2013

(54) ANTIEMETIC-ORAL CONTRACEPTIVE COMBINATION

(75) Inventors: Sheetal Kulkarni, Pune (IN); Srirupa Das, Pune (IN); Harshal Anil Jahagirdar, Pune (IN); Satish Dalal, Pune (IN); Shirish Kulkarni, Pune (IN)

(73) Assignee: Lupin Limited, Mumbai, Maharashtra (IN)

(*) Notice: Subject to any disclaimer, the term of this patent is extended or adjusted under 35 U.S.C. 154(b) by 276 days.

(21) Appl. No.: 12/739,880

(22) PCT Filed: Oct. 24, 2008

(86) PCT No.: PCT/IN2008/000704
§ 371 (c)(1),
(2), (4) Date: Apr. 26, 2010

(87) PCT Pub. No.: WO2009/054007
PCT Pub. Date: Apr. 30, 2009

(65) Prior Publication Data
US 2010/0240626 A1    Sep. 23, 2010

(30) Foreign Application Priority Data
Oct. 25, 2007    (IN) .......................... 1460/KOL/2007

(51) Int. Cl.
*A61K 31/56* (2006.01)
(52) U.S. Cl.
USPC .......................................... 514/170; 514/182
(58) Field of Classification Search
USPC ........................................................ 514/170
See application file for complete search history.

(56) References Cited

U.S. PATENT DOCUMENTS
6,156,742 A * 12/2000 Mackenzie .................. 514/170

FOREIGN PATENT DOCUMENTS
CA    2 354 250    1/2003
CN    1485093 A    3/2004

OTHER PUBLICATIONS

Ragan et al., "Metoclopramide pretreatment attenuates emergency contraceptive-associated nausea," *American Journal of Obstetrics and Gynecology* (2003) 188 (2): 330-333. XP-002515433.
Bagshaw et al., "Ethinyl oestradiol and D-Norgestrel is an effective emergency postcoital contraceptive: A report of its use in 1,200 patients in a family planning clinic," *The Australian and New Zealand Journal of Obstetrics & Gynecology* (1988) 28 (2): 137-140. XP-002515434.
Raymond et al., "Meclizine for prevention of nausea associated with use of emergency contraceptive pills: A randomized trial," *Obstetrics and Gynecology* (2000) 95 (2): 271-277. XP002515432.
Wellberry, C., "Emergency contraception," *Arch. Fam. Med.* (2000) 9: 642-646. XP002515431.
Form PCT/IB/373 for International Application PCT/IN2008/000704.
Form PCT/IB/326 for International Application PCT/IN2008/000704.
Form PCT/ISA/237 for International Application PCT/IN2008/000704.

* cited by examiner

*Primary Examiner* — San-Ming Hui
(74) *Attorney, Agent, or Firm* — Merchant & Gould P.C.

(57) ABSTRACT

The present invention relates to a method of reducing the incidence of nausea and vomiting associated with the administration of oral contraceptive formulation and a method of preparation of oral contraceptive formulation comprising progestin and/or estrogen and an antiemetic. The preferred oral contraceptive formulation comprises of levonorgestrel and an antiemetic.

6 Claims, No Drawings

US 8,507,465 B2

ANTIEMETIC-ORAL CONTRACEPTIVE COMBINATION

This application is a National Stage Application of PCT/IN2008/000704, filed Oct. 24, 2008, which claims benefit of Serial No. 1460/KOL/2007, filed Oct. 25, 2007 in India and which applications are incorporated herein by reference. To the extent appropriate, a claim of priority is made to each of the above disclosed applications.

FIELD OF THE INVENTION

The present invention relates to a method of reducing the incidence of nausea and vomiting associated with the administration of oral contraceptive formulation comprising progestin and/or estrogen and an antiemetic.

More particularly the present invention relates to oral contraceptive formulation comprising levonorgestrel and Ondansetron or meclizine.

The present invention relates to the method of preparation of oral contraceptive formulation comprising progestin and/or estrogen and an antiemetic.

BACKGROUND OF THE INVENTION

The ovarian/menstrual cycle is a complex event characterized by an estrogen rich follicular phase and, after ovulation, a progesterone rich luteal phase. Each has duration of approximately 14 days resulting in an intermenstrual interval of about 28 days. The endometrial tissue responds to the changes in hormonal milieu.

The onset of menstruation is the beginning of a new menstrual cycle and is counted as day 1. During a span of about 5 to 7 days, the superficial layers of the endometrium, which grew and developed during the antecedent ovarian/menstrual cycle, are sloughed because demise of the corpus luteum in the non-fertile menstrual cycle is associated with a loss of progesterone secretion. Ovarian follicular maturation occurs progressively resulting in a rise in the circulating levels of estrogen, which in turn leads to new endometrial proliferation.

The dominant ovarian follicle undergoes ovulation at mid-cycle, generally between menstrual cycle days 12 to 16 and is converted from a predominantly estrogen source to a predominantly progesterone source (the corpus luteum). The increasing level of progesterone in the blood converts the proliferative endometrium to a secretory phase in which the tissue proliferation has promptly abated, leading to the formation of endometrial glands or organs. When the ovulated oocyte is viably fertilized and continues its progressive embryonic cleavage, the secretory endometrium and the conceptus can interact to bring about implantation (nidation), beginning about 6 to 8 days after fertilization.

If an ongoing pregnancy is to be established via implantation, the embryo will attach and burrow into the secretory endometrium and begin to produce human chorionic gonadotropin (HCG). The HCG in turn stimulates extended corpus luteum function, i.e. the progesterone production remains elevated, and menses does not occur in the fertile menstrual cycle. Pregnancy is then established. In the non-fertile menstrual cycle, the waning level of progesterone in the blood causes the endometrial tissue to be sloughed. This starts a subsequent menstrual cycle.

Because endometrial proliferation serves to prepare the uterus for an impending pregnancy, manipulation of hormones and of the uterine environment can provide contraception. For example, estrogens are known to decrease follicle stimulating hormone secretion by feedback inhibition.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular which is believed to impede spermatozoal transport. Administration of progestin also inhibits luteinizing hormone secretion and blocks ovulation in humans.

Several devices and pharmaceutical compositions are available for the prevention of undesirable conception in the case of regular and planned coitus. For example, condom, pessary, intrauterine devices as well as the different mono- or multi-phasic oral contraceptives. The most prevalent form of oral contraception is a pill that combines an estrogen and/or a progestin, a so-called combined oral contraceptive preparation.

Further sometimes unintentional pregnancies occur for number of reasons. Certainly, they can occur following sexual intercourse when neither party uses a contraceptive device or drug. However, this is by no means, the only reason for unintended pregnancies. Condoms are known to break; diaphragms to slip; and traditional contraceptive pills are, by their own admission, not 100 percent effective, even when taken properly. Its use may also be justified following a rape and noncompliance with the dosing of oral contraceptives. Thus when pills are missed, particularly with the newer, low-dose products, the risk of pregnancy increases substantially. In fact, each year in the U.S. alone, approximately 750,000 pregnancies occur to women using traditional oral contraceptive regimens. Of course, some of these pregnancies occur because the patient has failed to completely and dogmatically follow the prescribed pharmaceutical regimen.

Emergency contraceptive ("EC") pills are an available treatment for women who are concerned they may have become pregnant by their most recent unprotected sexual encounter. These pills are intended for administration within days, and preferably within hours after unprotected sex and often contain relatively high doses of for example, a progestin and/or an estrogen. Reports in the scientific literature describe other drugs, which may be effective for emergency contraception as well. Dosages and protocols will vary with the drug(s) used. However, in each case, the "pills" help to prevent pregnancy, i.e. either preventing a fertilized ovum from implanting in the lining of the uterus and/or depending on the timing of intercourse, preventing the sperm from fertilizing an egg. Usually one tablet of levonorgestrel 0.75 mg should be taken orally as soon as possible within 72 hours after unprotected intercourse. The second tablet should be taken 12 hours after the first dose. Efficacy is better if levonorgestrel is taken as directed as soon as possible after unprotected intercourse. Further 1.5 mg of levonorgestrel can also be administered at one time as an emergency contraceptive pill. But all such emergency contraceptive pills, which contain high doses of contraceptive hormone, are associated with high incidence of nausea and vomiting. Further if vomiting occurs within three hours of taking the tablet; another tablet of emergency contraceptive pill should be taken immediately.

Norgestrel and levonorgestrel, namely/the D isomer of norgestrel [.+-.-17.α.-13-ethyl-17-hydroxy-18,19-dinor-pregn-4-en-20-in-3-on] have been used in combined preparations as contraceptives for a long time. Further the dose range of levonorgestrel, as emergency contraceptive pill is 1.50 mg in single or divided doses.

Another common problem associated with oral contraceptives as well as an emergency contraceptive pill is the incidence of nausea, which occurs, in a significant percentage of patients. Women may experience vomiting and nausea as major side effect due to contraceptive. It had been observed that about 23.1% of patient experience nausea and 5.6% vomiting when 0.75 mg of levonorgestrel is administered. This is not only uncomfortable, but may also compromise the efficacy of the contraceptive as the associated vomiting may expel out the contraceptive pill. Certainly, a woman who has taken an emergency contraceptive pill and has had an adverse effect, is less likely to take the steps to assure efficacy, including taking more emergency contraceptive pills. The Yuzpe method is among the most common means of emergency contraception. The Yuzpe method requires the use of large quantities of both progestin and estrogen. Thus this method entails numerous side effects of which the most predominant are nausea (54-74%) and vomiting (24-30%) which causes nonobservance of the prescribed treatment by the patient. The concomitant use of a dimenhydrinate salt (100 mg) thirty to sixty minutes prior to the Yuzpe method results in either the prevention or the attenuation of the aforementioned side effects. But it becomes cumbersome for the patient to remember to take dimenhydrinate salt prior to administration of emergency contraceptive, which reduces patient compliance.

Chinese patent CN 1485093 discloses a combination of maxeran preparation and acyeterion.

Canadian patent CA2354250 disclose use of dimenhydrate salt for the prevention or attenuation of adverse side effects associated with the administration of high doses of female hormones along with Yuzpe method. This patent application does not reduce the amount of hormone treatment but just adds dimenhydrinate in its regimen. But the drawback of administration of dimenhydrinate is its sedation properties and it has 4-6 hours of duration.

Therefore, there remains a need for an improved oral contraceptive formulation which shows reduced incidence of nausea and vomiting associated with the administration of oral contraceptive and in turn increases the patient compliance. Further the drowsiness associated with prior art is also mitigated.

Further it has also been recommended in the current therapy that if vomiting occurs within three hours of taking the tablet; another tablet of emergency contraceptive pill should be taken immediately to prevent contraceptive failure. Thus the present invention also eliminates the need to administer second pill to substitute the expelled emergency contraceptive pill. This alleviates patient anxiety related to contraceptive failure and also reduces the chance of administration of another dose of oral contraceptive.

OBJECTS OF THE INVENTION

The object of the present invention is a pharmaceutical formulation to reduce the incidence of nausea and vomiting associated with administration of oral contraceptive comprising an oral contraceptive and an antiemetic or their pharmaceutically acceptable salt(s) and derivative(s) thereof.

Another object of the invention is a pharmaceutical formulation to reduce the incidence of nausea and vomiting associated with administration of oral contraceptive wherein the oral contraceptive is in delayed release form and antiemetic is in immediate release form.

Another object of the invention is use of a pharmaceutical formulation to reduce the incidence of nausea and vomiting associated with administration of oral contraceptive comprising an oral contraceptive and an antiemetic or their pharmaceutically acceptable salt(s) and derivative(s) thereof.

Yet another object of the present invention a process for the preparation of a pharmaceutical formulation to reduce the incidence of nausea and vomiting associated with administration of oral contraceptive hormone comprising an oral contraceptive and an antiemetic or their pharmaceutically acceptable salt(s) and derivative(s) thereof.

DETAILED DESCRIPTION OF INVENTION

The present invention provides an oral contraceptive formulation, which shows reduced incidence of nausea and vomiting, associated with oral contraceptive. The oral contraceptive formulation of the present invention comprises an antiemetic and oral contraceptive. The oral contraceptive used according to present invention is progestin and/or estrogen.

The term "delayed release" is used in its conventional sense to refer to a drug formulation in which there is a lag time provided between oral administration of a drug dosage form and the release of the drug there from. "Delayed release" may or may not involve gradual release of drug over an extended period of time, and thus may or may not be "sustained release.". However delayed release can be used interchangeably with prolonged release, programmed release, controlled release, timed release, extended release, sustained release and other such dosage forms.

By "pharmaceutically acceptable" is meant a carrier comprised of a material that is not biologically or otherwise undesirable.

As used herein, "pharmaceutically acceptable salts" refer to derivatives of the active wherein the active is modified by reacting it with an acid or base as needed to form an ionically bound pair. Examples of pharmaceutically acceptable salts include conventional non-toxic salts or the quaternary ammonium salt of the parent compound formed, for example, from non-toxic inorganic or organic acids. Suitable non-toxic salts include those derived from inorganic acids such as hydrochloric, hydrobromic, sulfuric, sulfamic, phosphoric, nitric, and others known to those of ordinary skill in the art. The salts prepared from organic acids such as amino acids, acetic, propionic, succinic, glycolic, stearic, lactic, malic, tartaric, citric, ascorbic, palmoic, maleic, hydroxymaleic, phenylacetic, benzoic, salicylic, sulfanilic, fumaric, oxalic, isethionic, and others known to those of ordinarily skilled in the art.

As used herein, "pharmaceutically acceptable derivative(s)" means the active in any of its modified forms but not limited to such as solvates, hydrates, enantiomers, polymorphs etc "Therapeutically effective amount" means that the amount of active agent, which halts or reduces the progress of the condition being treated or which otherwise completely or partly cures or acts palliatively on the condition. A person skilled in the art can easily determine such an amount by routine experimentation and with an undue burden.

The term "lag-time" refers to a time period wherein less than about 10%, more particularly substantially none, of the dose (drug) is released The amount of progestin and estrogen used in the present invention is in any 'therapeutically effective amount' that can be used in contraception.

Estrogens which may be used in the present invention include, for example, ethinyl estradiol, 17.β.-estradiol, 17.β.-estradiol-3-acetate, mestranol, conjugated estrogens, USP and estrone or salts thereof. Furthermore the natural estrogens can be used, e.g., estrone, estradiol or estriol, and the esters thereof, inter alias estradiol valerate. 17.α.-Ethinylestradiol and estradiol valerate are preferred. The amount of estrogen used is described herein as that which is "equivalent" in estrogenic potency to an amount of ethinyl estradiol. The equivalent estrogenic potency of an estrogen to ethinyl estradiol may be readily determined by one of ordinary skill in the art.

Progestogens which may be used in the present invention include, for example, progesterone and its derivatives such as 17-hydroxy progesterone esters and 19-nor-17-hydroxy progesterone esters, 17-α-ethinyl testosterone, 17-α-ethinyl-19-nortestosterone (norethindrone) and derivatives thereof, norethindrone acetate, norgestrel, norgestimate, desogestrel, levonorgestrel, medroxyprogesterone, dienogest. Other exemplary progestogens include demegestone, drospirenone, dydrogesterone, gestodene, medrogestone, medroxy progesterone and esters thereof. The amount of progestogen used is described herein as that which is "equivalent" in progestogenic potency to an amount of norethindrone acetate. The equivalent progestogenic potency of a progestogen to norethindrone acetate may be readily determined by one of ordinary skill in the art. The most preferable progestogen for the present invention is levonorgestrel and the preferable dose is 1.5 mg in single or divided doses.

Suitable antiemetic for the present invention includes dopamine antagonist, 5HT3 receptor antagonist, anticholinergics, antihistaminics, cannabinoids and other drugs, which have antiemetic effects. The dopamine antagonists include metoclopramide, droperidol, domperidone, perphenazine, prochlorperazine, promethazine, triflupromazine and the likes. 5HT3 antagonist includes ondansetron, granisetron, dolasetron, tropisetron, and the likes. Anticholinergic drugs used as antiemetics are hyoscine, scopolamine and the likes. Anti-histaminics as promethazine, meclizine, buclizine, and likes are used as antiemetic. The most preferable antiemetic is ondansetron or meclizine and the preferable dosage range is 1-50 mg. Other antiemetics which are used as OTC antiemetics can also be combined together with levonorgestrel to prepare a OTC emergency contraceptive formulation.

According to the methods of the invention, the method of reducing nausea and vomiting associated with administration of oral contraceptives includes as combination of progestin and anti emetic or estrogen and antiemetic or estrogen, progestin and antiemetic. The preferable method of invention is the combination of progestin and antiemetic. The preferred progestin is levonorgestrel and anti-emetic is ondansetron or meclizine. The formulation of the present invention comprises of combination of antiemetic and oral contraceptive hormone in immediate release. The present invention may also have antiemetic in immediate release or controlled release and oral contraceptive hormone in immediate or delayed release or controlled release or pulsatile release. The formulation may be manufactured by any of the standard manufacturing procedures.

Thus the present invention allows the administration of emergency contraceptive pill or any other formulation comprising an anti emetic, preferably ondansetron or meclizine or any other antiemetic, in immediate release or controlled release and progestin and/or estrogen, preferably levonorgestrel used in dose of 1.5 mg in single or divided doses, in immediate or delayed or controlled release form. The formulation needs to be administered as soon as possible after unprotected intercourse, however when the dose of levonorgestrel is 0.75 mg the second dose is to be taken after 12 hours of taking the first dose.

According to one other method of the present invention the formulation may comprise of an antiemetic preferably ondansetron or meclizine or any other antiemetic, in immediate or controlled release and progestin and/or estrogen, preferably levonorgestrel used in dose of 1.5 mg in single or divided doses, in pulsatile release in such a way that the oral contraceptive is released in pulses.

According to one other method of the present invention the formulation may comprise of an antiemetic preferably ondansetron or meclizine or any other antiemetic, in immediate or controlled release and progestin and/or estrogen, preferably levonorgestrel preferably used in dose of 1.5 mg in single or divided doses, in controlled release form.

According to one other method of the present invention the formulation may comprise of an antiemetic preferably ondansetron or meclizine or any other antiemetic, in immediate or controlled release and progestin and/or estrogen, preferably levonorgestrel preferably used in dose of 1.5 mg as single or divided doses, in delayed release form. The antiemetic is released prior to release of oral contraceptive hormone.

According to the one of the method of the invention an oral contraceptive combination with reduced incidence of nausea and vomiting comprise of an antiemetic in immediate release formulation and progestin and/or estrogen in delayed release formulation. It is preferred that antiemetic is released at least about 30 minutes prior to the release of oral contraceptive hormones. Preferably the release of antiemetic is about one hour prior to the release of oral contraceptive hormones. This reduces the incidence of nausea and vomiting associated with the administration of oral contraceptive formulation, which in turn increases patient compliance, and efficacy of oral contraceptive formulation and emergency contraceptive pill.

The oral pharmaceutical formulation useful in this invention may be in any orally acceptable dosage form including, but not limited to granules, sachets, capsules, matrix tablets, layered tablet, coated tablets and the like.

The immediate-release portion of the formulation according to present invention may be either a coating applied or deposited over the entire surface of a unitary delayed-release core, or a single layer of a tablet constructed in two or more layers, one of the other layers being the delayed-released portion or in the form of granules admixed with delayed release granules. Further the formulation may be in the form plurality of delayed release and immediate release granules, which may be compressed or filled in capsules along with other pharmaceutical excipients. Immediate release of the drug from the immediate-release portion is achieved in any of a variety of ways. One example is by placing the drug in a layer or coating that is sufficiently thin to allow fast penetration by gastrointestinal fluid, which then leaches the drug at a rapid rate. Another example is by incorporating the drug in a mixture that includes a supporting binder or other inert material that dissolves readily in gastrointestinal fluid, releasing the drug as the material dissolves. A third is the use of a supporting binder or other inert material that rapidly disintegrates into fine particles upon contact with gastrointestinal fluid, with both the binder particles and the drug quickly dispersing into the fluid. Examples of materials that rapidly disintegrate and disperse are lactose and microcrystalline cellulose. Hydroxypropylmethylcellulose is a component that can serve both as a suspending agent and as a binder.

The immediate-release drug can thus be deposited as a suspension or a solution over a unitary core of the delayed-release drug, which may optionally be coated with the intermediate layer. Deposition can be achieved by coating techniques commonly used in the pharmaceutical formulation art, such as spraying, pan coating, and the like. Alternatively, the immediate-release drug can be combined with particles of a binding matrix and compressed over a preformed layer of the delayed-release drug to form a layered tablet. In either case, the immediate-release coating or layer separates relatively quickly from the remainder of the tablet after ingestion, leaving the remainder intact. The formulation may have delayed release granules/pellets and immediate release granules/pellets compressed in tablet or filled in capsule.

Dosage forms with delayed release portion may be manufactured using standard manufacturing procedures. The formulation may be prepared into granules or may be coated with delayed release polymers. A delayed release coating can be applied to a tablet, tablet segment, bead, granule, caplet or capsule using a coating pan, an airless spray technique, fluidized bed coating equipment, or the like. The coating thickness, as noted above, must be sufficient to ensure that the oral contraceptive hormone is releases after the release of antiemetic. The "coating weight", or relative amount of coating material per dosage unit, generally dictates the time interval between ingestion and drug release. The preferred coating weights for particular coating materials may be readily determined by those skilled in the art by evaluating individual release profiles for tablets, beads and granules prepared with different quantities of various coating materials.

Such procedures are known to those skilled in the art. The formulations of the present invention may comprise of excipients known in the art. The polymers may include hydrophlic and/or hydrophobic polymer as cellulose derivative as hydroxypropylmethyl cellulose, methyl cellulose, ethyl cellulose, polysaccharides, gums, the polymerized gelatin, cellulose butyrate phthalate, cellulose hydrogen phthalate, cellulose propionate phthalate, polyvinyl acetate phthalate, cellulose acetate phthalate, cellulose acetate trimellitate, hydroxypropyl methylcellulose phthalate, hydroxypropylmethylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof preferably formed from acrylic acid, methacrylic acid, methyl acrylate, ethyl acrylate, methyl methacrylate, ethyl methacrylate, and/or other vinyl monomers. Preferred enteric polymers are acrylic acid and methacrylic acid polymers and copolymers, particularly those that are commercially available under the trade names Eudragit® L and Eudragit® S, in which the ratio of free carboxyl to ester groups is about 1:1 and 1:2, respectively, and wherein each copolymer has a (weight average) molecular weight of about 135,000 Da.

The delayed release dosage units in any of the embodiments of the invention can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials are comprised of bioerodible, gradually hydrolyzable, gradually water-soluble, and/or enzymatically degradable polymers, and preferred delayed release coatings are comprised of enteric coating materials.

The coating may contain a plasticizer to prevent the formation of pores and cracks that would permit the penetration of the gastric fluids. Suitable plasticizers include, but are not limited to, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

Alternatively, a delayed release dosage unit may be formulated by dispersing an active agent within a matrix of a suitable material such as an delayed coating material or other delayed release polymeric materials.

Other additives may be incorporated in the formulation, such as diluents, binders, lubricants, antioxidants, colorings, sweeteners, flavorings and acidulants, wetting agents, hydrophilizing agents such as sorbitol and cyclodextrins, osmotic agents or pore forming agents such as mannitol, pH correctors, stabilizing agents such as trehalose and mannitol, adsorbants, chelating and sequestering agents and gastroresistant film-coating excipients of the type including cellulose acetylphthalate and polymethacrylates. By way of example, there may be chosen any one of the following diluents or alternatively a combination thereof: calcium carbonate, calcium sulfate, sucrose, dextrin, dextrose, dicalciumphosphate-dihydrate, kaolin, magnesium carbonate, magnesium oxide, maltodextrin, cellulose, microcrystalline cellulose, sorbitol, starches, pregelatinized starch, talc, tricalciumphosphate and lactose. Among the binders, there may be mentioned: gum arabic, gum tragacanth, guar gum, alginic acid, sodium alginate, sodium carboxymethylcellulose, dextrin, gelatin, hydroxyethylcellulose, hydroxypropylcellulose, liquid glucose, magnesium and aluminium silicate, maltodextrin, povidone, pregelatinized starch, starch and zein. The lubricants are glidants (such as anhydrous colloidal silica, magnesium trisilicate, magnesium silicate, cellulose, starch, talc or tricalcium phosphate) or alternatively antifriction adhering agents (such as calcium stearate, glyceryl monostearate, glyceryl palmitostearate, hydrogenated vegetable oils, paraffin, magnesium stearate, polyethylene glycol, sodium benzoate, sodium lauryl sulfate, fumaric acid, stearic acid or zinc stearate and talc).

As examples of antioxidants, persons skilled in the art may select any of the following compounds: ascorbic acid, ascorbyl palmitate, fumaric acid, propyl gallate, sodium ascorbate and sodium metabisulfite, α-tocopherol, malic acid, BHA and BTH. Preferred wetting agents are: sodium docusate and sodium lauryl sulfate which are anionic surfactants; benzalkonium chloride, benzethonium chloride and cetrimide which are cationic surfactants; glyceryl monooleate, fatty acid esters of polyoxyethylene sorbitan, poly(vinyl alcohol) and sorbitans, which are nonionic surfactants. Among the pH regulators, there are acidifying agents of the type including citric acid, hydrochloric acid, lactic acid, tartaric acid, as well as alkalinizing agents of the type including monoethanolamine, diethanolamine and triethanolamine, potassium citrate, sodium bicarbonate, sodium citrate dihydrate.

Examples of adsorbents are bentonite, anhydrous colloidal silica, kaolin, magnesium and aluminium silicate, microcrystalline cellulose and cellulose. As chelating and sequestering agents, there may be used citric acid monohydrate, edetic acid, disodium phosphate, monosodium phosphate, potassium citrate, tartaric acid and sodium citrate dihydrate.

The quantities of these additives are those normally used in the art.

The formulation of the present invention may be prepared by conventional techniques well known to those skilled in the art such as wet granulation, melt granulation, direct compression or dry compaction and/or slugging and the like. The invention is illustrated by the following non-limiting examples:

Example 1

| Sr. No. | Ingredients | Qty. (mg/tab.) |
|---|---|---|
| | Levonorgestrel Tablet | |
| | Part A: Levonorgestrel Tablet | |
| 1 | Levonorgestrel | 0.75 |
| 2 | Povidone | 1.80 |
| 3 | Lactose | 41.25 |
| 4 | Crospovidone | 15.00 |
| 5 | Aerosil | 0.60 |
| 6 | Magnesium stearate | 0.60 |
| | Eudragit Coating | 1-5% |
| | Part B: Meclizine Hydrochloride granules | |
| 1 | Meclizine Hydrochloride | 25 |
| 2 | Povidone | 6.5 |
| 3 | Dicalcium phosphate | 84.2 |
| 4 | Starch | 13 |
| 5 | Mg-stearate | 1.3 |

Procedure:
Part A:—Levonorgestrel Tablet
1. Lactose, Crospovidone, Aerosil were sifted.
2. Povidone and Levonorgestrel were dissolved in DCM
3. Step 1 was granulated using step2. & dried
4. Finally Step 3 was lubricated with Mg-stearate.
5. Finally blend was compressed using appropriate punch.
6. Above tablet was coated with Eudragit coating solution.

Part B: Meclizine Granules
1. Meclizine Hydrochloride, Dicalcium phosphate, starch were sifted.
2. Povidone was dissolved in water.
3. Step 1 was granulated with step 2.
4. Finally Step 3 was lubricated with Mg-stearate.

The above tablets & granules are filled in suitable size capsules

Example 2

| Sr. No. | Ingredients | Qty. (mg/tab.) |
|---|---|---|
| | Part A: Levonorgestrel Tablet | |
| 1 | Levonorgestrel | 1.50 |
| 2 | Povidone | 1.80 |
| 3 | Lactose | 40.50 |
| 4 | Crospovidone | 15.00 |
| 5 | Aerosil | 0.60 |
| 6 | Mg-stearate | 0.60 |
| 7 | DCM | QS |
| | Ethyl cellulose Coating | 1-5% |
| | Part B: Meclizine Hydrochloride granules | |
| 1 | Meclizine Hydrochloride | 25 |
| 2 | Povidone | 6.5 |
| 3 | Dicalcium phosphate | 84.2 |
| 4 | starch | 13 |
| 5 | Mg-stearate | 1.3 |

Procedure:
Part A:—Levonorgestrel Tablet
1. Lactose monohydrate, Crospovidone and aerosil were sifted using suitable sieve.
2. Povidone and Levonorgestrel were dissolved in DCM
3. Step 1 was granulated using step 2.& dried
4. Finally Step 3 was lubricated with Mg-stearate.
5. Finally blend was compressed using appropriate punch.
6. Above table was coated with Ethyl cellulose coating solution.

Part B: Meclizine Granules
1. Meclizine Hydrochloride, Dicalcium phosphate, starch were sifted through #40
2. Povidone was dissolved in water.
3. Step 1 was granulated with step 2.
4. Finally Step 3 was lubricated with Mg-stearate.

The Above tablets & granules are filled in suitable size capsules.

Example 3

| Sr. no | Ingredients | Mg/per 2 Tablets |
|---|---|---|
| | Part A: -Levonorgestrel Tablet | |
| 1. | Levonorgestrel | 0.75 |
| 2. | Starch | 91 |
| 3. | Lactose | 71.80 |
| 3. | Povidone | 5 |
| 4. | Methylene chloride | q.s |
| | Lubrication | |
| 5. | Starch | 7.0 |
| 6. | Colloidal silicon dioxide | 0.6 |
| 7. | Magnesium stearate | 0.6 |

Procedure:
1) Dissolve required qty. of drug in required quantity of Methylene chloride. Stir it, until clear solution was obtained, then add povidone, followed by stirring until it forms a clear solution.
2) Starch and Lactose were sifted and granulated with above binder solution, dried and lubricated. Lubricated blend then compressed into two tablets.

Coating
Finally the tablets were coated with the below coating solution.

| Sr. no | Ingredients | Weight |
|---|---|---|
| | Coating Formula | |
| 1. | Eudragit | 100 g |
| 2. | Talc | 9 g |
| 3. | TEC | 6 g |
| 3. | Water | 110 g |

Procedure:
1) Disperse Talc and TEC in Water.
2) Add Eudragit in step 1 and stir for 15 min.
3) Levonorgestrel Tablets were coated using dispersion of step 2

| Sr. no | Ingredients | Mg/tab |
|---|---|---|
| | Part B: - Meclizine Hydrochloride Granules | |
| 1. | Meclizine Hydrochloride | 25 |
| 2. | Dicalcium Phosphate | 50 |
| 3. | Sucrose | 44 |

-continued

Part B: - Meclizine Hydrochloride Granules

| Sr. no | Ingredients | Mg/tab |
|---|---|---|
| 4. | Polyethylene glycol | 15 |
| 5. | Starch | 2 |
| 6. | Magnesium steareate | 1 |

Procedure:

1) Meclizine Hydrochloride, DCP, Sucrose, PEG were sifted using suitable sieve.

2) Slurry of the starch was prepared by dissolving in required qty. of water, then added in to the boiling water under stirring and paste was prepared and then cooled at room temperature.

3) Sifted materials of the first step 1 were then granulated with the above starch paste. Granules were dried followed by lubrication of granules.

Part C:—Capsule Filling

Two tablets of levonorgestrel and Meclizine Hydrochloride granules were filled in the capsule of suitable size.

Example 4

Part A: -Levonorgestrel Tablet

| Sr. no | Ingredients | Mg/tab |
|---|---|---|
| 1. | Levonorgestrel | 0.75 |
| 2. | Starch | 91 |
| 3. | Lactose | 71.80 |
| 3. | Povidone | 5 |
| 4. | Methylene chloride | q.s |
| | Lubrication | |
| 5. | Starch | 7.0 |
| 6. | Colloidal silicon dioxide | 0.6 |
| 7. | Magnesium steareate | 0.6 |

Procedure:

1) Dissolve required qty. of drug in required quantity of DCM. Stir it, until clear solution is obtained and then add povidone. Stir it until it forms a clear solution.

2) Starch and Lactose were sifted and granulated with above binder solution followed by drying and lubrication.

3) Lubricated blend was then compressed using suitable punch

Part B: - Coating solution of Meclizine Hydrochloride

| Sr. no | Ingredients | mg/tab |
|---|---|---|
| 1. | Meclizine Hydrochloride | 25 |
| 2. | Opadry | 5 |
| 3. | IPA | 84 |
| 4. | DCM | 56 |

Procedure:

Dissolve required qty. of Opadry in IPA and DCM mixture and stir it until it forms a clear solution, and then add required qty. of Meclizine Hydrochloride to form a clear solution.

Part C:—Meclizine Hydrochloride loading on Levonorgestrel tablet Levonorgestrel tablets are then coated with Meclizine Hydrochloride solution above.

Example 5

Part A: -Levonorgestrel Tablet

| Sr. no | Ingredients | Mg/tab |
|---|---|---|
| 1. | Levonorgestrel | 0.75 |
| 2. | Starch | 91 |
| 3. | Lactose | 71.80 |
| 3. | Povidone | 5 |
| 4. | Methylene chloride | q.s |
| | Lubrication | |
| 5. | Starch | 7.0 |
| 6. | Colloidal silicon dioxide | 0.6 |
| 7. | Magnesium stearate | 0.6 |

Procedure:

Binder Preparation

Drug was dissolved in DCM and was stirred until a clear solution was obtained followed by addition of povidone while stirring to obtain a clear solution Granulation Starch and Lactose were sifted using a suitable sieve and granulated with above binder solution followed by drying and sifting of the granules.

Lubrication

Sifted granules were then lubricated with Mg-stearate.

Part B: - Meclizine Hydrochloride Tablets

| Sr. no | Ingredients | Mg/tab |
|---|---|---|
| 1. | Meclizine HCL | 25 |
| 2. | Dicalcium Phosphate | 125 |
| 3. | Sucrose | 88 |
| 4. | Polyethylene glycol | 30 |
| 5. | Starch | 4 |
| 6. | Magnesium stearate | 2 |

Procedure:

1) Meclizine Hydrochloride, DCP, Sucrose, PEG was sifted using suitable sieve.

2) Starch paste was prepared and then cooled at room temperature.

3) Sifted materials of the step 1 was then granulated with the above starch paste, followed by drying and sifting of granules. Sifted granules were further lubricated using magnesium stearate.

Part C:—Compression

Tablet in tablet formulation of Levonorgestrel and Meclizine was prepared using the granules of Part A and B by compressing using suitable punch.

Example 6

| Part A: -Levonorgestrel Tablet | | |
|---|---|---|
| Sr. no | Ingredients | Mg/tab |
| 1. | Levonorgestrel | 0.75 |
| 2. | Starch | 91 |
| 3. | Lactose | 56.05 |
| 4. | Hypromellose | 15 |
| 5. | Povidone | 5 |
| 6. | Methylene chloride | q.s |
| | Lubrication | |
| 7. | Starch | 7.0 |
| 8. | Colloidal silicon dioxide | 0.6 |
| 9. | Magnesium steareate | 0.6 |

Procedure:

1) Drug was dissolved in DCM and was stirred until a clear solution was obtained followed by addition of povidone while stirring to obtain a clear solution.

2) Starch, Lactose and Hypromellose were sifted and granulated with above binder solution followed by drying and sieving.

3) Sifted granules were then lubricated with Mg-stearate.

| Part B: - Meclizine Hydrochloride Tablets | | |
|---|---|---|
| Sr. no | Ingredients | Mg/tab |
| 1. | Meclizine HCL | 25 |
| 2. | Dicalcium Phosphate | 125 |
| 3. | Sucrose | 88 |
| 4. | Polyethylene glycol | 30 |
| 5. | Starch | 4 |
| 6. | Magnesium stearate | 2 |
| | Total | 274 |

1) Meclizine Hydrochloride, DCP, Sucrose and PEG were sifted using a suitable sieve.

2) Starch paste is prepared.

3) Sifted materials of the step 1 was then granulated with the above starch paste followed by drying and sifting.

4) Sifted dried granules were then lubricated with Mg-stearate.

Part C:—Compression

Bilayer tablet formulation of Levonorgestrel and Meclizine Hydrochloride was prepared using granules of Part A and B by compressing using a suitable punch.

Example 7

| Part A: - Delayed Release Pellets of Levonorgestrel | | |
|---|---|---|
| Sr. no | Ingredients | For 100 g of pellets |
| 1. | Levonorgestrel | 0.75 |
| 2. | Starch | 4.25 |
| 3. | Lactose | 90.0 |

-continued

| Part A: - Delayed Release Pellets of Levonorgestrel | | |
|---|---|---|
| Sr. no | Ingredients | For 100 g of pellets |
| 4. | Povidone | 5.00 |
| 5. | Methylene chloride | Q.S. |

Procedure:

1. Drug was dissolved in Methylene chloride and was stirred until a clear solution was obtained followed by addition of povidone while stirring to obtain a clear solution.

2. Starch and Lactose were sifted and granulated with binder solution of step 1.

32. Wet mass of step 1 was passed through Extruder, then passed through spheronizer and pellets were prepared.

4. Finally the dried Pellets were coated with below coating solution.

| Coating Formula: - | | |
|---|---|---|
| Sr. no | Ingredients | % w/w |
| 1. | Ethyl cellulose | 3.5 |
| 2. | TEC | 0.175 |
| 3. | Ethanol | 96.5 |

Procedure

TEC was dissolved in Ethanol under stirring followed by addition of Ethylcellulose to obtain a clear solution.

| Part B: - Immediate Release Pellets of Meclizine Hydrochloride | | |
|---|---|---|
| Sr. no | Ingredients | For 150 g. |
| 1. | Meclizine HCL | 25 |
| 2. | Dicalcium Phosphate | 50 |
| 3. | Microcrystalline Cellulose | 50 |
| 3. | Sucrose | 10 |
| 4. | Polyethylene glycol | 10 |
| 5. | Povidone | 5 |

Procedure:

1. Meclizine Hydrochloride, DCP and microcrystalline cellulose were sifted and granulated with Povidone binder solution containing Sucrose and Polyethylene glycol 2. Wet mass then passed through Extruder, then passed through spheronizer and pellets were prepared.

3. Finally the Pellets were dried.

The pellets of Part A and B are filled in capsules

Example 8

| Part A: -Levonorgestrel Tablet | | |
|---|---|---|
| Sr. no | Ingredients | Mg/per 2 Tablets |
| 1. | Levonorgestrel | 0.75 |
| 2. | Starch | 91 |
| 3. | Lactose | 71.80 |
| 3. | Povidone | 5 |
| 4. | Methylene chloride | q.s |

-continued

| Part A: -Levonorgestrel Tablet | | |
|---|---|---|
| Sr. no | Ingredients | Mg/per 2 Tablets |
| | Lubrication | |
| 5. | Starch | 7.0 |
| 6. | Colloidal silicon dioxide | 0.6 |
| 7. | Magnesium stearate | 0.6 |

Procedure:

1) Dissolve required qty. of drug in required quantity of Methylene chloride. Stir it, until clear solution was obtained, then add povidone, followed by stirring until it forms a clear solution.

2) Starch and Lactose were sifted and granulated with above binder solution, dried and lubricated. Lubricated blend then compressed into two tablets.

Coating

Finally the tablets were coated with the below coating solution.

| Coating Formula | | |
|---|---|---|
| Sr. no | Ingredients | Weight |
| 1. | Eudragit | 100 g |
| 2. | Talc | 9 g |
| 3. | TEC | 6 g |
| 3. | Water | 110 g |

Procedure:

1) Disperse Talc and TEC in Water.
2) Add Eudragit in step 1 and stir for 15 min.
3) Levonorgestrel Tablets were coated using dispersion of step 2

| Part B: - Ondansetron Granules | | |
|---|---|---|
| Sr. no | Ingredients | Mg/tab |
| 1. | Ondansetron | 8 |
| 2. | Microcystalline cellulose | 123 |
| 3. | Crospovidone | 5 |
| 6. | Magnesium stearate | 1 |

Procedure:

1) Ondansetron, Microcystalline cellulose and crospovidone were sifted using a suitable sieve and uniformly mixed.
2) Magnesium stearate was sifted using suitable sieve and step 1 was lubricated, to obtain the lubricated powder blend.

Part C:—Capsule Filling

Two tablets of levonorgestrel and ondansetron blend were filled in the capsule of suitable size.

Dissolution

The dissolution of the present invention is carried out using USP Type I Apparatus (Basket) at 100 RPM. The dissolution of the invention is carried out in 0.1 NHcl for first 2 hours followed by 6.8 Phosphate buffer using 0.1% SLS. The tablet formulation was placed in the apparatus and dissolution was periodically measured. The in vitro dissolution studies of Example 3 is as shown below:

TABLE 1

| Dissolution Profile of Example 3 is as follows | |
|---|---|
| Time (min) | Cumulative % drug release |
| Meclizine granules in 0.1N HCl | |
| 0 | 0 |
| 10 | 47.3 |
| 20 | 75.1 |
| 30 | 85.6 |
| Levonorgestrel tablets 6.8 Phosphate buffer | |
| 0 | 0 |
| 10 | 39.1 |
| 15 | 94.3 |
| 20 | 95.8 |

Other technologies known to those skilled in the art can be used in order to achieve immediate release of antiemetic and delayed release of oral contraceptive for the present invention.

The invention claimed is:

1. An oral pharmaceutical formulation comprising a combination of levonorgestrel and an antiemetic selected from ondansetron or meclizine within the same formulation, wherein levonorgestrel is contained in a delayed release portion comprising at least one delayed release agent selected from the group consisting of hydrophilic or hydrophobic polymers or mixtures thereof, and the antiemetic is contained in an immediate release portion comprising at least one pharmaceutically acceptable excipients, wherein at least 80% of antiemetic is released within 30 min in 0.1 N HCl and at least 80% of levonorgestrel is released within 30 min at pH 6.8, when the dissolution is carried out for 2 hours in 0.1 N HCl followed by pH 6.8 phosphate buffer using a USP Type I apparatus at 100 rpm.

2. The oral pharmaceutical formulation according to claim 1 wherein the antiemetic is selected from ondansetron or meclizine is released at least about 30 minutes prior to the release of Levonorgestrel.

3. The oral pharmaceutical formulation according to claim 1 is selected from the group consisting of granules, sachets, capsules, matrix tablets, layered tablet or coated tablets.

4. The oral pharmaceutical formulation according to claim 1 wherein the levonorgestrel is coated with a delayed release agent selected from an enteric polymer.

5. The oral pharmaceutical formulation according to claim 1 wherein the dose of levonorgestrel is selected from 0.75 mg or 1.5 mg.

6. A method of emergency contraception comprising administering the single oral pharmaceutical formulation according to claim 1 as an emergency contraceptive.

* * * * *